United States Patent
Don Michael

(10) Patent No.: US 10,258,455 B2
(45) Date of Patent: Apr. 16, 2019

(54) APPARATUS AND PROCEDURE FOR TRAPPING EMBOLIC DEBRIS

(71) Applicants: Don Michael International, LLC, Bakersfield, CA (US); Sharmini Don Michael, Bakersfield, CA (US)

(72) Inventor: T. Anthony Don Michael, Bakersfield, CA (US)

(73) Assignee: DON MICHAEL INTERNATIONAL, LLC, Bakersfield, CA (US)

( * ) Notice: Subject to any disclaimer, the term of this patent is extended or adjusted under 35 U.S.C. 154(b) by 640 days.

(21) Appl. No.: 14/784,089

(22) PCT Filed: Apr. 11, 2014

(86) PCT No.: PCT/US2014/033744
§ 371 (c)(1),
(2) Date: Oct. 13, 2015

(87) PCT Pub. No.: WO2014/169176
PCT Pub. Date: Oct. 16, 2014

(65) Prior Publication Data
US 2016/0058540 A1      Mar. 3, 2016

Related U.S. Application Data

(60) Provisional application No. 61/811,425, filed on Apr. 12, 2013.

(51) Int. Cl.
*A61F 2/01* (2006.01)
*A61F 2/24* (2006.01)

(52) U.S. Cl.
CPC ............ *A61F 2/013* (2013.01); *A61F 2/2436* (2013.01); *A61F 2230/0006* (2013.01); *A61F 2230/0067* (2013.01); *A61F 2230/0093* (2013.01)

(58) Field of Classification Search
CPC .................. A61F 2/013; A61F 2/2436; A61F 2230/0093; A61F 2230/0067; A61F 2230/0006
See application file for complete search history.

(56) References Cited

U.S. PATENT DOCUMENTS

| 5,947,995 A | 9/1999 | Samuels et al. |
| 7,585,321 B2 | 9/2009 | Cribier |

(Continued)

FOREIGN PATENT DOCUMENTS

WO      2009002548 A1    12/2008

*Primary Examiner* — Anh T Dang
(74) *Attorney, Agent, or Firm* — Browdy and Neimark, P.L.L.C.

(57) ABSTRACT

Apparatus for implanting a heart valve and removing debris from a blood vessel, composed of: a collapsible and deployable filter for blocking debris in a blood vessel in a patient's body; a circular cuff coupled to a small diameter end of the filter and defining a through passage extending from the small diameter end, the cuff having, at a first end, an internal diameter coaxial with a circular opening at the small diameter end of the filter; a first sheath for housing the filter in its collapsed state and having a length sufficient to extend out of a patient's body when the filter is at a desired location in a blood vessel; and an assembly for implanting a prosthetic valve in the patient's heart, said assembly comprising a second sheath and a catheter housed in the second sheath and carrying an implantable valve.

10 Claims, 3 Drawing Sheets

(56) References Cited

U.S. PATENT DOCUMENTS

2006/0100658 A1* 5/2006 Obana .................... A61F 2/013
                                                   606/200
2009/0082857 A1   3/2009  Lashinski et al.
2011/0313445 A1  12/2011  Galdonik et al.
2013/0289716 A1  10/2013  Don Michael

* cited by examiner

APPARATUS AND PROCEDURE FOR TRAPPING EMBOLIC DEBRIS

BACKGROUND OF THE INVENTION

The present invention relates to an apparatus and procedure for aiding medical treatments in the blood circulation system of a patient, and in particular for preventing the circulation of embolic debris, or blood clots, resulting from such treatments. The invention is primarily, but not exclusively, concerned with providing protection in connection with procedures like those for implanting a prosthetic heart valve.

There are known procedures, known as transcatheter aortic valve implantation (TAVI), in which a prosthetic heart valve is implanted at the site of a defective native valve, or of a previously implanted defective prosthetic valve. In these procedures, the new prosthetic valve and its guiding structure are introduced by a transcutaneous catheterization technique. For example, for implanting a prosthetic aortic heart valve, the valve and delivery components may be introduced through an incision in the groin or arm and along a blood vessel path to the desired location.

Such a procedure is disclosed, for example, in U.S. Pat. No. 7,585,321, which issued to Alan Cribier on Sep. 8, 2009, the entire disclosure of which is incorporated herein by reference. Such valves and their associated guiding devices are marketed by Medtronic and by Edwards Lifesciences, one example of the Edwards valves being marketed under the trade name Sapien.

Although such prosthetic valves have been used successfully to provide a replacement for stenotic native heart valves or defective prosthetic valves, known implantation procedures can result in the creation of embolic debris, which will flow downstream through the circulatory system and will, in a certain percentage of cases, cause blockages in smaller blood vessels.

This adverse result can be alleviated by associating the TAVI assembly with an emboli filter, as disclosed in copending U.S. application Ser. No. 13/835,816, the disclosure of which is incorporated herein by reference.

BRIEF SUMMARY OF INVENTION

The present invention provides an apparatus and procedure to prevent the circulation of embolic debris resulting from procedures carried out in the blood circulatory system, one such procedure being, for example, the implantation of a prosthetic heart valve, while facilitating introduction of the apparatus into the patient's body.

The components of embodiments of the invention may be conveyed to the treatment site along various blood vessel paths and may all be introduced via the same path. For example, if the components are to be positioned in, or pass through, the aorta, the, or each, component can be introduced through an incision in a groin and the associated femoral artery, or through an incision in an arm and the associated subclavian artery predicated on the available sizes of the filter and TAVI device.

DETAILED DESCRIPTION OF THE INVENTION

Figure 1:
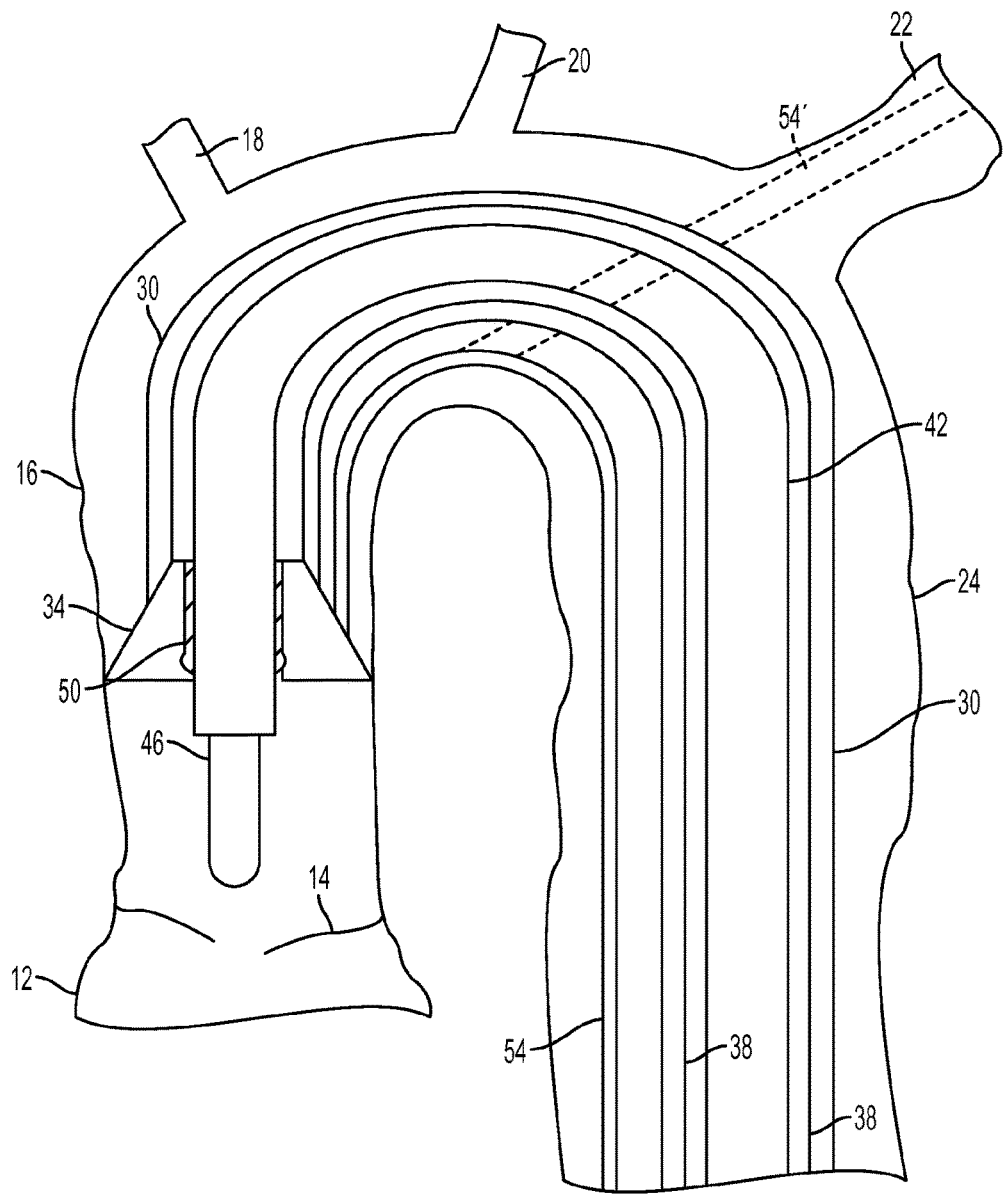
FIG. 1 is a simplified pictorial view of an embodiment of apparatus according to the present invention.

FIG. 1 is a representation of the portions of the circulatory system that are relevant to the present invention. These include the heart left ventricle 12, the aortic valve 14, the ascending aorta 16, the innominate artery 18, the carotid artery 20 on the left side, the subclavian artery 22 on the left side and the descending aorta 24. Descending aorta 24 communicates with the iliacs (not shown in FIG. 1) that lead to the right and left femoral arteries that are accessible through the groin.

The apparatus according to the invention includes a first sheath 30, a collapsible and deployable filter 34 provided with control wires 38, a second sheath 42 for guiding a valve implantation assembly 46 and as is conventional in the art, a guide wire (not shown) that will be introduced through sheath 42 and through the aortic valve to guide subsequent positioning of assembly 46. Prior to deployment, filter 34 may be collapsed within sheath 30, possibly at the distal end thereof and filter 34 is deployed prior to valve implantation.

Filter 34 is provided with an axially extending cuff 50, to be described in detail below.

The apparatus according to the invention may further include a small diameter catheter 54 intended to supply contrast fluid to the region of valve 14 in order to aid positioning of assembly 46. Catheter 54 may be introduced along the same blood vessel path as the other components of the apparatus, or, alternatively, as shown in broken lines 54', through, for example, the left subclavian artery.

In the performance of a procedure according to the invention, first sheath 30 is introduced through an incision in the groin, the femoral artery, descending aorta 24 and ascending aorta 16 to a location such as shown in FIG. 1. During this insertion, filter 34 is housed in a collapsed state within first sheath 30, possibly adjacent the distal end of that sheath. Then, while holding filter 34 in position with the aid of control wires 38, first sheath 30 is retracted by a distance sufficient to enable filter 34 to expand to bring the large diameter, open lower end of filter 34 into contact with the entire periphery of the artery wall. The large diameter lower end of filter 34 is preferably located at the mid area of the ascending aorta, and not either the level of the aortic valve or at a level just below innominate artyery 18. Then, second sheath 42 is introduced through first sheath 30 and is extended through cuff 50 of filter 34. Then, the guide wire (not shown) is introduced through sheath 42, far enough to pass through the aortic valve. Then, valve assembly 46 is introduced through second sheath 42 and is extended out of second sheath 42, guided by the guide wire, and is positioned to implant a prosthetic valve at the location of valve 14. During this procedure, contrast fluid may be introduced into the treatment region through catheter 54 to aid positioning of valve assembly 46.

Upon completion of the implantation procedure, which is carried out in a conventional manner, second sheath 42 and assembly 46 are withdrawn, while debris resulting from the implantation procedure is trapped by filter 34 or flows through the passage provided by cuff 50 into sheath 30. This debris may be collected at the proximal end of sheath 30 along with blood, as will be described in greater detail below.

When essentially all debris has been trapped in either filter 34 or withdrawn through first sheath 30, filter 34 is retracted into sheath 30, and sheath 30, with filter 34 housed therein, is withdrawn from the patient's body, together with sheath 42 and valve assembly 46.

The apparatus could also be introduced along a path defined by a slit in the arm and the corresponding subclavian artery, depending on the available sizes of these structures.

Sheath 42 preferably has a diameter not greater than 5 mm and assembly 46 is of a type having a diameter of 3-4 mm.

Figure 2:
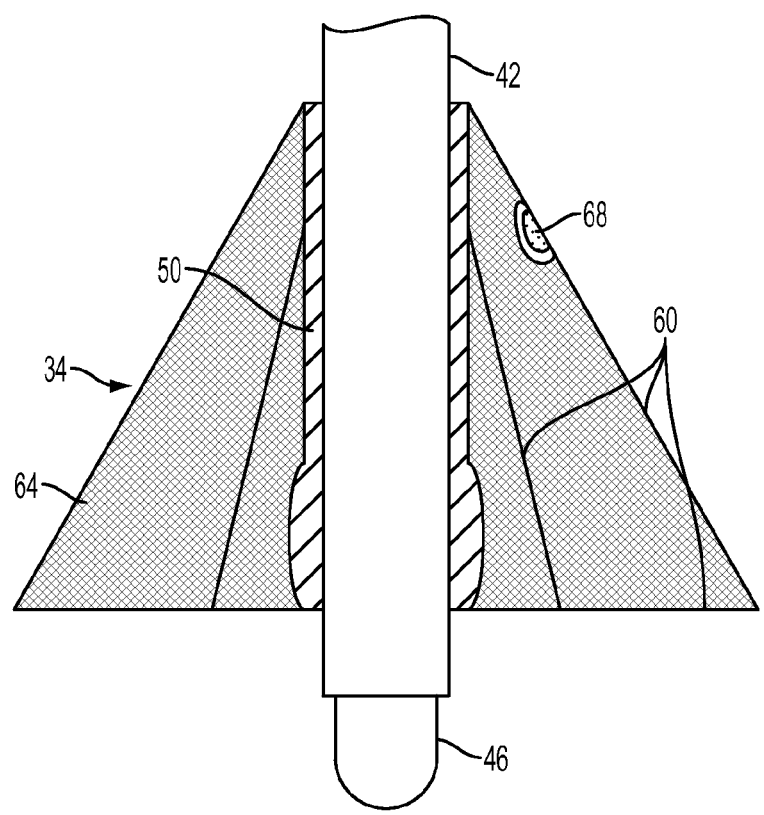
FIGS. 2 and 3 are simplified cross-sectional views of a filter and associated components of a heart valve delivery system.

FIG. 2 illustrates one embodiment of a filter 34 forming a component of apparatus according to the invention. Filter 34 is composed of a wire framework 60 made of a memory metal such as nitinol, and a filter fabric 64 of appropriate pore size to trap debris while allowing the passage of blood, supported by framework 60.

Filter 34 has a generally conical structure with a small diameter end, at the top in FIG. 2, and a large diameter end, at the bottom in FIG. 2. Framework 60 is composed of a small diameter ring at the top, a large diameter ring at the bottom and an appropriate number of longitudinal struts between the rings. In addition, at least the rings may be made radiopaque to assist proper positioning of filter 34 in the aorta. In the expanded state of filter 34, the diameter of the small diameter end can be of the order of 4-6 mm, and preferably 4-5 mm, and the maximum diameter of the large diameter end can be of the order of 30-40 mm.

According to a presently preferred embodiment of the invention, the large diameter end of filter 34 is formed to have a generally oval shape with a major diameter of about 40 mm and a minor diameter of the order of 30 mm. This allows the lower end of the filter to better conform to the somewhat oval shape of a normal aorta.

Of course, the dimensions of filter 34 can be varied to conform to aortas having different sizes, for example in children.

Filter 34 may be provided with a side opening 68 in which filter fabric is not present. Side opening 104 is closed by a series of flaps of a suitable material, constructed to normally be closed. Side opening 68 is provided to receive catheter 54 so that the catheter can be advance to a point where its distal, or outlet, end is in the vicinity of aortic valve 14.

Alternatively, side opening 68 need not be provided and catheter 54 can be advanced to the desired location between filter 34 and aorta 16.

Cuff 50 is cylindrical and coaxial with the longitudinal axis of deployed filter 34 and may be secured to the small diameter ring of framework 60. Cuff 50 extends from the small diameter end of filter 34 to the center of the open large diameter end and defines a through passage having a diameter of the order of 3-5 mm and preferably 3-4 mm.

Cuff 50 will not extend beyond the opening, i.e., the large diameter end, of filter 34. The through passage in cuff 50 is dimensioned to allow sheath 42 to enter the through passage with ease and to be guided toward the location of the heart valve and ventricle. Filter 34 and cuff 50 are arranged so that their longitudinal axes extend substantially parallel to one another and point, to the extent possible, toward the center of valve 14.

Cuff 50 is constructed to be stable and relatively stiff. The through passage in cuff 50 preferable tapers at least slightly from the top to the bottom of filter 34 to allow sheath 42 to be inserted easily into that passage while being guided by the lower portion of the passage. This will help to facilitate the valve implantation procedure since multiple attempts may be needed to position and implant the valve. Cuff 50 also helps to prevent the motion of sheath 42 from being transmitted to the filter and from destabilizing it.

Cuff 50 is preferably constructed of polymeric material and is dimensioned to be larger than the valve assembly by an amount sufficient to prevent friction from interfering with deployment of the valve assembly. For a valve assembly that is 3 to 4 mm in diameter, filter 34 should have a radially compressed diameter of at least 4-5 mm to enable the large diameter end of the filter to assume the required deployed, radially expanded, diameter of 32-40 mm.

Cuff 50 preferably has an increased wall thickness at its lower end, as shown, to help restrict lateral motion of sheath 42.

The stability of filter 34 is maintained by the laterally expanded large diameter end, which exerts pressure against the wall of the aorta. Since the aorta pulsates, the filter will have to be in constant contact, both when the heart pumps during systole and when the heart relaxes during diastole.

The filter is further stabilized by allowing the first sheath 30 to be held against the top of filter 34 such that upward motion of the filter can be prevented. This is accomplished by advancing sheath 30, if necessary, to hold filter 34 in place.

Figure 3:
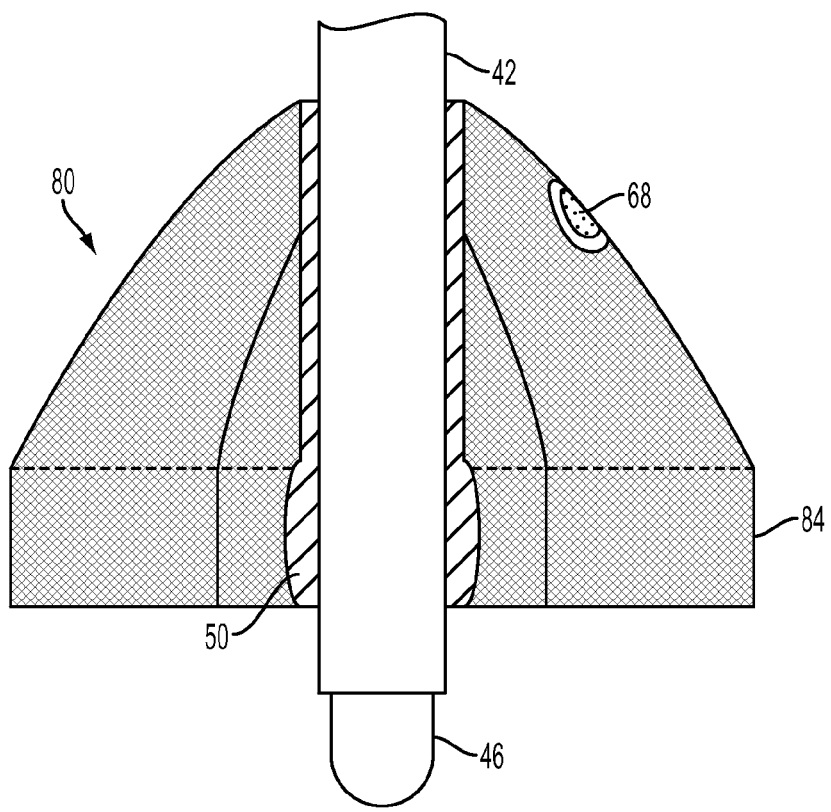

FIG. 3 is a view similar to that of FIG. 2 of a novel filter 80 according to the invention, which may be used in the apparatus according to the invention in place of filter 34.

Filter 80 differs from filter 34 essentially by being provided, adjacent its large diameter end, with a cylindrical peripheral wall portion 84. The purpose of this peripheral wall portion is to increase the contact area between filter 80 and the aorta wall, and will be particularly useful in the case of so-called porcelain aorta, which is calcification of the aorta wall that reduces, and can even eliminate, the flexibility of the aorta, and thus its ability to confirm to the shape of the large diameter end of a filter.

Preferably, cylindrical peripheral wall portion 84 will have a longitudinal length, in the direction between the small diameter end and the large diameter end of filter 80, of at least 3 mm.

Figure 4:
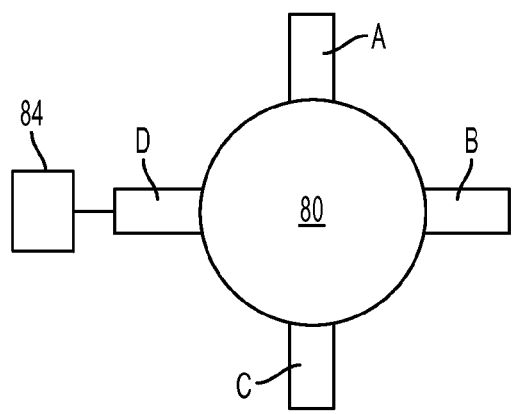
FIG. 4 is a pictorial view of a further component of an apparatus according to the present invention.

A further component of apparatus according to the present invention is a multi-position valve 80, shown in FIG. 4. Valve 80 preferably has four ports A, B, C and D and is constructed, in a manner known in the art, to either block port A, or to connect port A to any one of ports B, C and D.

Port A is configured to be removably connected in a sealed manner to the proximal end of sheath 30 when the other components of the apparatus, 34, 38 and 42 are not present within sheath 30.

Port B may be placed in communication with port A at the beginning of a procedure, before components 34, 38 and 42 have been introduced, and port B may be connected to a source of anticoagulant to be delivered, if needed, if needed to the vicinity of valve 14. Port C can be attached to a pressure monitor and placed in communication with port A to measure the pressure within sheath 30 after withdrawal of sheath 42 and valve implantation assembly 46.

At the end of a procedure, after components 34, 38 and 42 have been withdrawn from sheath 30, port A of valve 80 will be reconnected to sheath 30 and port D will be placed in communication with port A to allow blood and debris to flow to a filter 84. Filtered blood may then be returned to a blood vessel in the patient's body.

Valve 80 also has a position in which port A is blocked.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. Apparatus for implanting a prosthetic heart valve and removing debris from a blood vessel, comprising:
    a collapsible and deployable filter for blocking debris and passing blood in a blood vessel in a patient's body, said filter comprising;
        a framework of a flexible material, said framework being constructed to have a radially compressed state, in which said framework is radially compressed by radial deforming forces, and a radially expanded state; and
        a flexible filter material secured to said framework and having pores dimensioned to prevent the passage of debris therethrough while allowing the passage of blood, wherein:
        said filter having, in the radially expanded state of said framework, a generally conical or frustoconical form with a large diameter end, a small diameter end opposite to said large diameter end, and a side surface extending between said large diameter end and said small diameter end;
        said flexible filter material covers at least a major part of said side surface;
        said large diameter end is open to receive blood and debris and is dimensioned to prevent flow of blood between said large diameter end and the blood vessel wall when said framework is in the radially expanded state,
        said small diameter end is provided with a circular opening having a given diameter, and
        said filter further comprises a cuff having a circular cross-section, said cuff having a first end coupled to said small diameter end of said filter and defining a through passage extending from said small diameter end toward said large diameter end, and said cuff having, at said first end, an internal diameter equal to the given diameter and coaxial with said circular opening at said small diameter end of said filter;
    a first sheath having a free end and an internal diameter selected to house said filter in the radially compressed state, said sheath having a length sufficient to extend out of a patient's body when said filter is at a desired location in a blood vessel;
    an assembly for implanting a prosthetic valve in the patient's heart, said assembly comprising a second sheath and a catheter housed in said second sheath and carrying an implantable valve,
    wherein said second sheath has an outer diameter not greater than said given diameter and is insertable through said circular opening at said small diameter end of said filter and through said through passage defined in said cuff.

2. The apparatus of claim 1, wherein at least a portion of said framework of said filter comprises a radiopaque material.

3. The apparatus of claim 1, wherein said side surface of said filter has a cylindrical portion extending from said large diameter end.

4. The apparatus of claim 1, wherein said cuff extends to a location proximate to said large diameter end of said filter and is dimensioned and operative to guide said second sheath to the location where the prosthetic heart valve is to be implanted.

5. The apparatus of claim 1, wherein said given diameter of said circular opening is 4-6 mm.

6. The apparatus of claim 5, further comprising:
    a tube having a distal end insertable to a location where the prosthetic valve is to be implanted and a proximal end, and having a length sufficient to enable said proximal end to extend out of a patient's body when said filter is at a desired location in the blood vessel; and
    a source of contrast fluid connectable to said tube.

7. The apparatus of claim 6, wherein said filter further comprises at least one control wire having a distal end connected to said framework at the small diameter end of said filter.

8. The apparatus of claim 6, further comprising:
    a second filter connected to said proximal end of said tube for separating debris conveyed through said tube from blood conveyed through said tube.

9. A procedure for implanting a prosthetic aortic valve in the patient's heart while blocking flow of debris through the aorta, comprising:
    providing the apparatus of claim 8,
    inserting said collapsible and deployable filter, in its radially compressed state in said first sheath, along a blood vessel path into the aorta;
    withdrawing said sheath by a distance sufficient to cause said filter to extend from said fee end and assume the radially expanded state at a desired location on the aorta, while said free end of said first sheath contacts said filter in the radially expanded state;
    inserting said assembly for implanting a prosthetic aortic valve in the patient's heart into the aorta through said circular opening, said cuff and said large diameter end of said filter;
    operating said assembly to implant the prosthetic aortic valve;
    withdrawing said assembly from the patient's body;
    conveying debris resulting from said inserting and operating steps through said first sheath from the region enclosed by said filter to a location outside the patient's body; and
    withdrawing said assembly from the patient's body.

10. The procedure of claim 9, further comprising supplying contrast medium through said tube to the location where the valve is implanted.

* * * * *